(12) United States Patent
Keith et al.

(10) Patent No.: US 8,185,485 B2
(45) Date of Patent: May 22, 2012

(54) DEVICE FOR ANALYZING THERMAL DATA BASED ON BREAST SURFACE TEMPERATURE FOR THE DETECTION FOR USE IN DETERMINING CANCEROUS CONDITIONS

(75) Inventors: Louis G. Keith, Chicago, IL (US); William H. Reeves, Coral Springs, FL (US); Jimmy D. Holmes, Reno, NV (US); Rajendra Acharya U, Singapore (SG); Yin Kwee Ng, Singapore (SG)

(73) Assignee: Lifeline Biotechnologies, Inc., Reno, NV (US)

( * ) Notice: Subject to any disclaimer, the term of this patent is extended or adjusted under 35 U.S.C. 154(b) by 938 days.

(21) Appl. No.: 12/198,967

(22) Filed: Aug. 27, 2008

(65) Prior Publication Data

US 2010/0056944 A1    Mar. 4, 2010

(51) Int. Cl.
*G06F 17/00* (2006.01)
(52) U.S. Cl. .................. 706/45; 600/474; 600/549
(58) Field of Classification Search .......... 706/45; 600/474, 549
See application file for complete search history.

(56) References Cited

U.S. PATENT DOCUMENTS

| | | | | |
|---|---|---|---|---|
| 3,877,463 | A * | 4/1975 | Cary et al. ................ | 600/549 |
| 3,995,621 | A * | 12/1976 | Fletcher et al. ........... | 600/474 |
| 5,301,681 | A * | 4/1994 | DeBan et al. ............. | 600/549 |
| 5,810,010 | A * | 9/1998 | Anbar ...................... | 600/474 |
| 5,820,263 | A * | 10/1998 | Ciobanu .................. | 374/111 |
| 5,941,832 | A * | 8/1999 | Tumey et al. ............. | 600/549 |
| 5,961,466 | A * | 10/1999 | Anbar ...................... | 600/474 |
| 5,999,843 | A * | 12/1999 | Anbar ...................... | 600/474 |
| 6,023,637 | A * | 2/2000 | Liu et al. ................. | 600/474 |
| 6,067,371 | A | 5/2000 | Gouge et al. | |
| 6,389,305 | B1 | 5/2002 | Deban et al. | |
| 2004/0002663 | A1 | 1/2004 | Reeves | |
| 2007/0213617 | A1 * | 9/2007 | Berman et al. ........... | 600/473 |
| 2008/0004904 | A1 | 1/2008 | Tran | |
| 2010/0056947 | A1 * | 3/2010 | Holmes ................... | 600/549 |

OTHER PUBLICATIONS

Szu, H.; Kopriva, I.; Hoekstra, P.; Diakides, N.; Diakides, M.; Buss, J.; Lupo, J.; , "Early tumor detection by multiple infrared unsupervised neural nets fusion," Engineering in Medicine and Biology Society, 2003. Proceedings of the 25th Annual International Conference of the IEEE , vol. 2, no., pp. 1133- 1136 vol. 2, Sep. 17-21, 2003.*

Koay, J.; Herry, C.; Frize, M.; , "Analysis of breast thermography with an artificial neural network," Engineering in Medicine and Biology Society, 2004. IEMBS '04. 26th Annual International Conference of the IEEE , vol. 1, no., pp. 1159-1162, Sep. 1-5, 2004.*

* cited by examiner

*Primary Examiner* — Alan Chen
*Assistant Examiner* — David H Kim
(74) *Attorney, Agent, or Firm* — SilverSky Group, LLC

(57) ABSTRACT

A device for providing improved classification of breast tissue wherein the tissue is classified as one of cancerous and non-cancerous tissue includes sensors for sensing temperature of a subject breast tissue over a predetermined period and generating signals in response thereto and a computer operatively connected to the sensors for receiving and manipulating the signals operatively associated with a normalizer for applying a normalization to each the signal by a function of X/Y where X is one temperature reading of one of the signals for a particular subject and Y is the maximum temperature obtained from a predetermined number sets of temperature readings obtained a plurality of subject breast tissue from the subject to provide a set of normalized signals used by a trained artificial classifier to produce a signal indicative of cancerous and non-cancerous tissue of the subject.

8 Claims, 10 Drawing Sheets

Graphical User Interface (GUI) for detection and classification of breast cancer

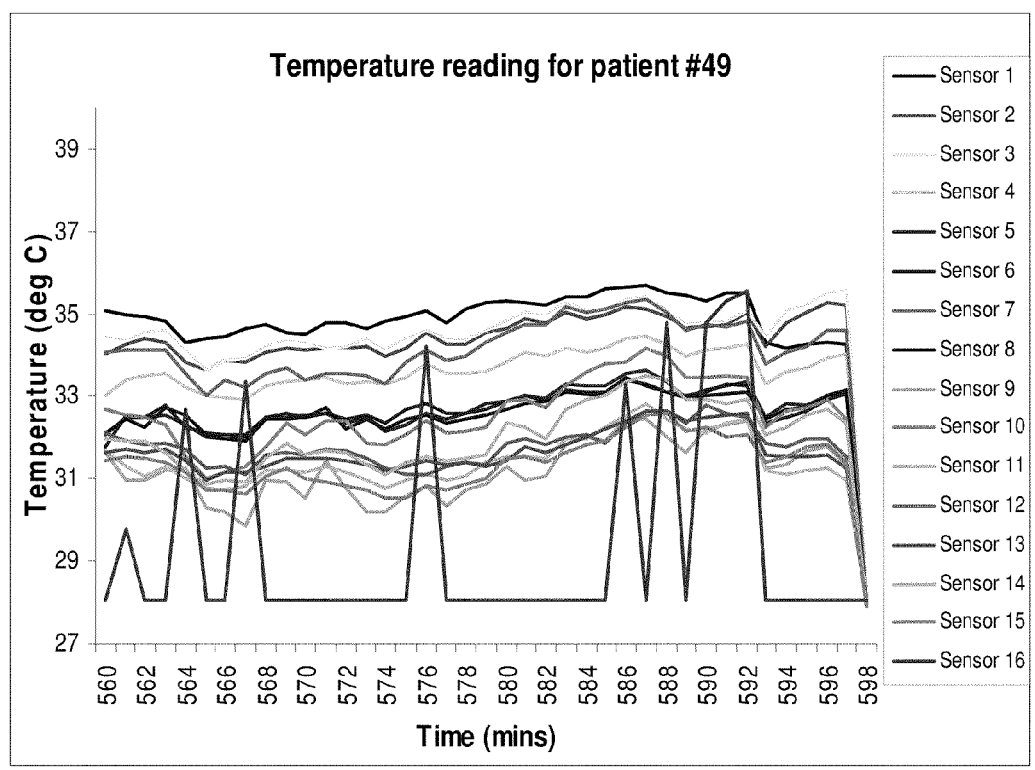
FIGURE 3 Drastic fluctuations of the temperature in several sensors for patient #1001.

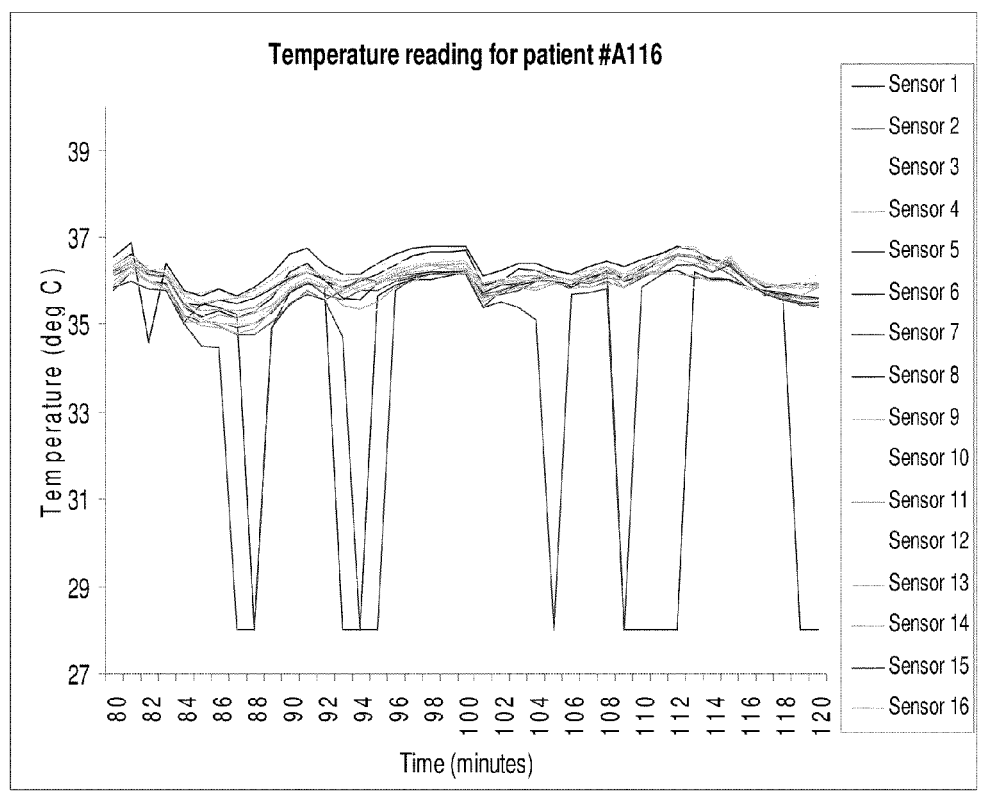
FIGURE 4 Drastic fluctuations of the temperature in several sensors for patient #A116.

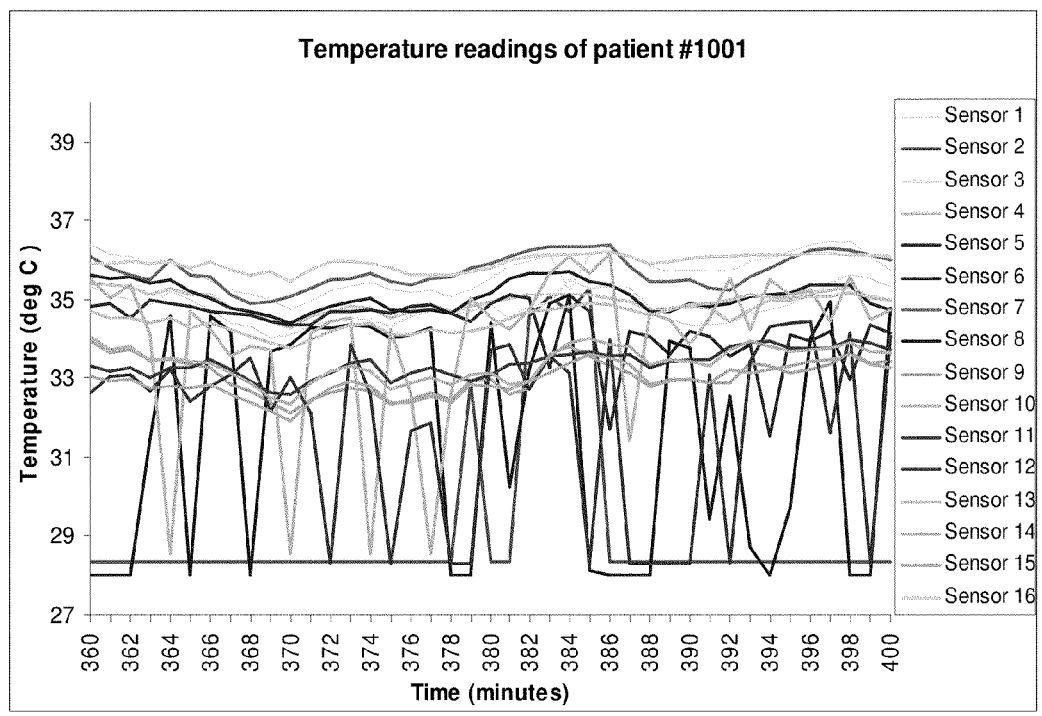
FIGURE 5 All sensors having their temperatures plunge to the lower values.

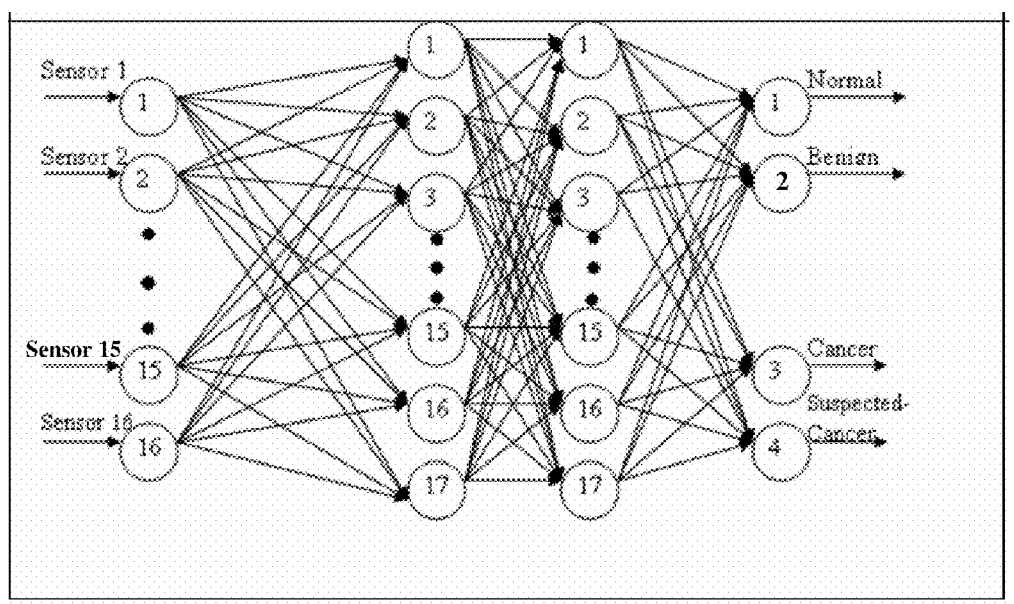
FIGURE 6 Feed-forward classifier used for the 4 classifications.

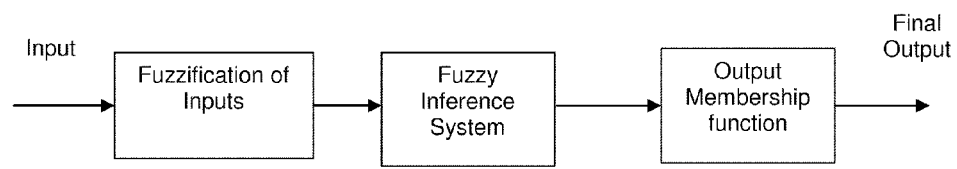
FIGURE 7 Fuzzy classification system.
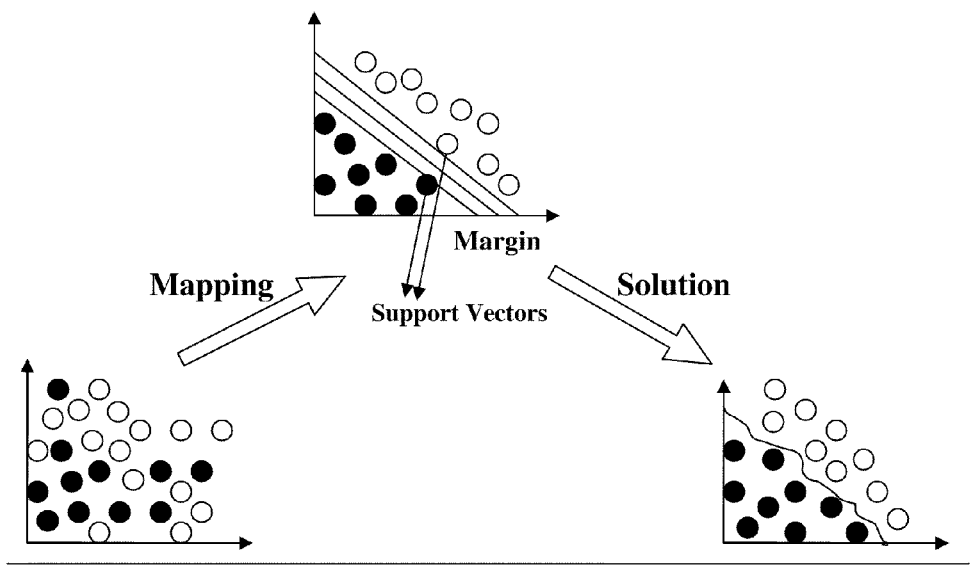
FIGURE 8 An overview process on SVM algorithm.

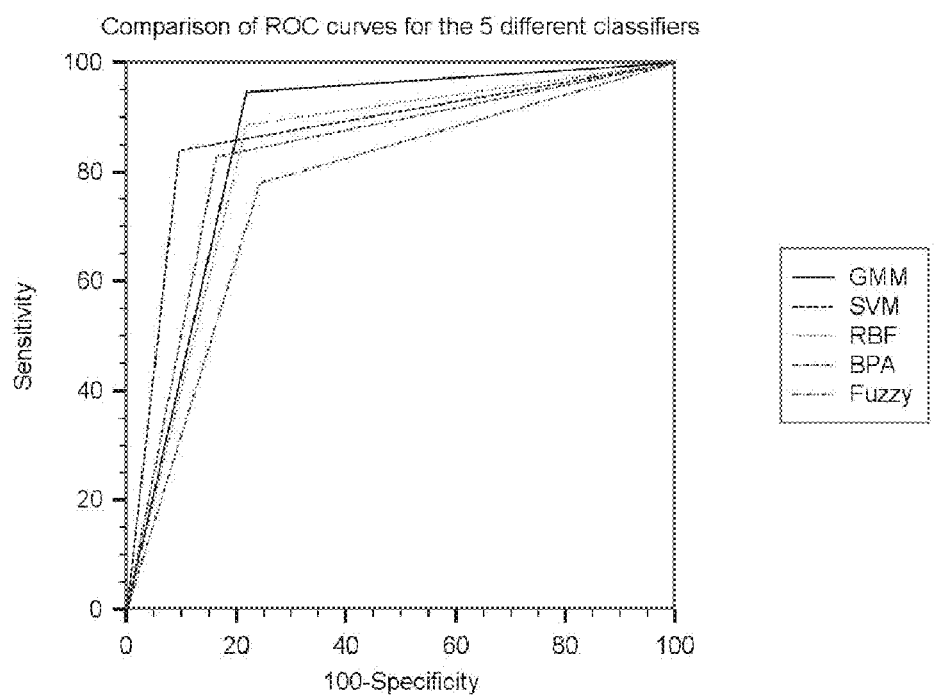
FIGURE 9 Comparison of ROC curves for the five classifiers.

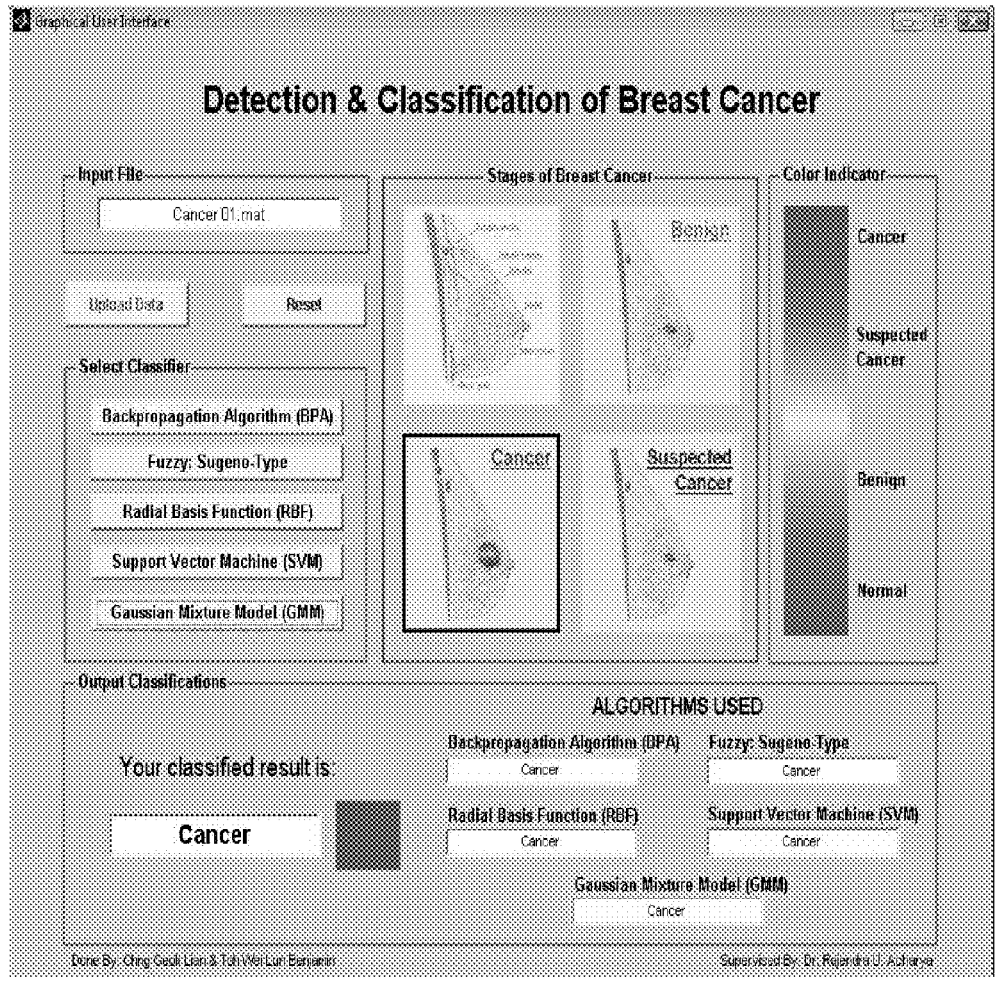
FIGURE 10 Graphical User Interface (GUI) for detection and classification of breast cancer

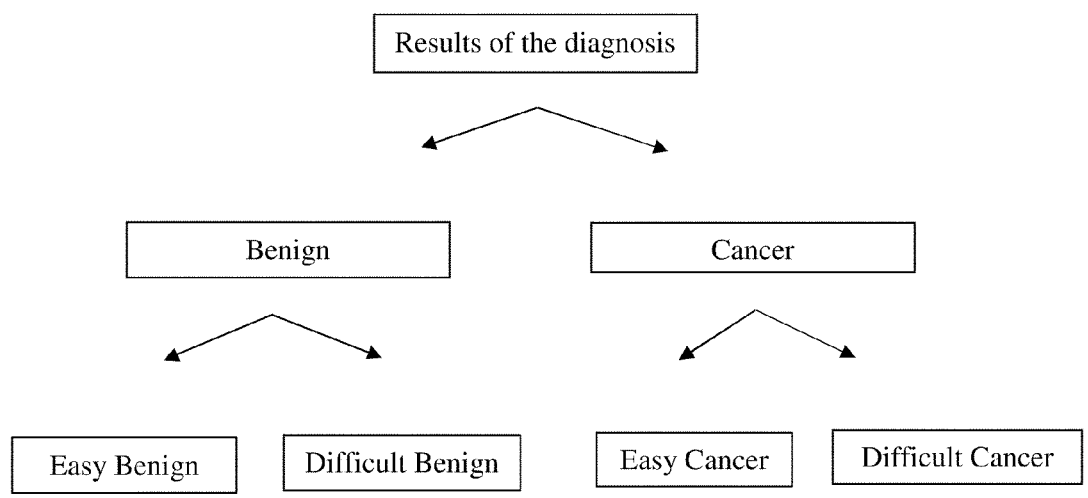
FIGURE 11 depicts sample files are grouped according to patient's illness namely easy benign, difficult benign, easy cancer and difficult cancer.

DEVICE FOR ANALYZING THERMAL DATA BASED ON BREAST SURFACE TEMPERATURE FOR THE DETECTION FOR USE IN DETERMINING CANCEROUS CONDITIONS

FIELD OF INVENTION

The present invention relates to a device which indicates abnormal physiological conditions, and more particularly to, but not by way of limitation, a device for analyzing thermal data based on breast surface temperature for the detection for use in determining cancerous conditions.

BACKGROUND

Breast Cancer continues to be the second leading cause of death for women between the ages of 40 to 55 in America. The number of women developing breast cancer has increased tremendously from 1:20 in 1960 to 1:7 today. Epidemiological studies estimate that one in eight women will develop breast cancer during their lifetimes. Moreover, one in five women with breast cancer will die of the disease despite the considerable advances in treatment. According to the American Cancer Society, in 2007, an estimated 178,480 new cases and 40,460 deaths from breast cancer in women are expected to occur in the United States. Given these circumstances, early detection of breast cancer is considered an important prognostic factor, and it has aptly suggested that death from malignancy rather than its detection should be the point of reference in evaluating any screening program.

Breast cancer occurs when cells in the breast begin to grow out of control and can invade nearby tissues or spread throughout the body. It is one of the leading causes of cancer death in women. Cancer development appears to generate an increase in the temperature on the breast surface. There are limitations of mammography as a screening modality, especially in young women with dense breasts and therefore there is a need to develop of novel and more effective screening strategies with a high sensitivity and specificity.

For several decades medical researchers around the world have struggled to find an accurate method for unraveling the nuances of the interpretation of thermal circadian data related to tumor growth in the breast as a detection modality. It has been felt by many researchers that cracking the thermal data code of the breast's minute incremental changes in the breast's temperatures which take place over a twenty-four hour period are direct reflections of the breast's physiological activity and tumor growth.

Currently, mammography is considered the gold standard as a screening tool for the early detection of breast cancer. Unfortunately, it is a standard that does not always shine brightly, for wide variations exist in its sensitivity and specificity in published reports. Mammographic sensitivity varied from 100% in fatty breasts to 4% in extremely dense breasts, as evidenced by a recent study. Moreover, its limitations in young and premenopausal women with dense breast tissue strengthen the need to develop new modalities for the early detection of breast cancer, especially in this group of vulnerable patients. To this end, magnetic resonance imaging (MRI) has been shown to be more sensitive in the early detection of occult breast cancers, particularly in pre-menopausal women for whom the sensitivity of mammography is compromised, but with less specificity. Additional modalities are still under development, such as electrical impedance scanning (EIS), mammary ductoscopy (MD) and proteomics of nipple aspirate fluid (NAF) and serum. In spite of these advances women in the United States are subjected to a million unnecessary breast biopsies each year, because of the inadequacies of the aforementioned breast cancer detection modalities' inability to separate benign from cancerous lesions.

It is known that the establishment and growth of most tumors depend on the successful recruitment of new blood vessels into and around the tumor cells. This latter process, also known as angiogenesis, is dependent on the production of angiogenic growth factors by the tumor cells. Because these new vessels lack smooth muscle fibers rendering them unreceptive to control by hormone control, a more constant blood flow to the area increases the local temperature in the area surrounding the tumor than found in normal breast tissue.

It is recognized that the breast exhibits a circadian rhythm that is reflective of its physiology. The relationship between breast skin temperature and breast cancer has been documented and it is found that the differences between the characteristics of rhythmic changes in skin temperature of clinically healthy and cancerous breasts were real and measurable.

The superficial thermal patterns measured on the surface of the breast are most likely related to tissue metabolism and visualization within the underlying tissue. Such thermal patterns change significantly as a result of normal phenomena including the menstrual cycle, pregnancy and, more importantly, the pathologic process itself. Additionally, it is generally stated that cancer development, in most instances, represents the summation of a large number of mutations that occur over years, each with its own particular histologic phenotype that can be seen in pre-menopausal mastectomy specimens. Cancer development appears to generate its own thermal signatures, and the complexity or lack thereof may be a reflection of its degree of development.

Radiologists fail to detect cancer in up to thirty percent of patients with breast cancer. Also, the malignancies missed by the radiologists are evident in two thirds of the mammograms. There is a need to further assist radiologists, surgeons and other physicians in detecting, diagnosing, successfully biopsing and operating on precancerous and cancerous conditions.

It is known that areas of mammalian tissue adjacent to carcinomas exhibit increased temperature from that exhibited contemporaneously by non-adjacent, non-cancerous areas. The temperature of the cancer-affected areas can fluctuate several degrees Centigrade from normal tissue; these differences having been demonstrated while monitoring such areas for a 24-hour period (one circadian cycle).

One prior device used for detecting cancer is a brassiere which includes a plurality of temperature sensors, an analog multiplexer circuit, a control circuit, a sample and hold circuit, an analog/digital converter, a buffer register, a storage register, a clock and a data logger. The device allows for the storage of temperature readings in a digital form. This digital data may be uploaded to the data logger which converts the digital signals to decimal form so that the temperature differences may be read and analyzed by a supervising physician and the problems associated with such devices are stated in commonly owned U.S. Pat. No. 6,389,305.

Other devices use a passive thermographic analytical apparatus provide a direct readout of the results through analysis of a thermographic radiation pattern of the human body. As previously recognized, such devices are unable to detect small tumors on the order of less than 0.5 cm and possibly other larger tumors as well, especially certain types of cancers and do not take into account the chaotic fluctuation of normal body temperatures over time and between locations on the body.

As previously mentioned, one common and widely used technique for determining existence of breast cancer is mammography. This radiological technique is invasive and not desirable. Most cancer is diagnosed too late and successful diagnosis and treatment are more attainable if the cancer is found at early stages. Other commonly owned devices as described in U.S. Pat. Nos. 6,389,305, 5,941,832, 5,301,681 have met with some limited success, but have yet to provide an optimal breast cancer detection device. There remains a need to improve the method and device for detection of potentially cancerous conditions in breasts.

By virtue of the instant invention, an understanding of the pathological observations and recent technological advances have facilitated the recording of these thermal circadian rhythm variations of the breast in a manner which renders an improved and useful breast cancer detection device.

Recently new modalities, such as magnetic resonance imaging (MRI), have been shown to be more sensitive in the early detection of occult breast cancers, particularly in premenopausal women in whom the sensitivity of mammography is compromised. In the recent reports, MRI is able to detect cancer in the contralateral breast that were missed by mammography or in clinical examination at the time of the initial breast examination. In addition, MRI has proved to be a better screening tool for women with genetic mutations in BRCA1 or BRCA2 genes, and in those women with a strong family history of breast cancer. Although the sensitivity of MRI is better than that of mammography, the technique is flawed by a lower specificity and a far greater expense. However, recently, the American Cancer Society announced a change in its breast cancer screening recommendation guidelines, recommending that women with high genetic risk (such as those who have mutation in the BRCA1 or BRCA2 genes or those with a strong family history of breast cancer) be screened with magnetic resonance imaging.

The breast has been recognized to exhibit circadian rhythms which are reflections of its underlying physiology. There now exist a body of evidence that these rhythms associated with malignant cell proliferation are largely non-circadian. Others have examined the relationship between breast skin temperature and breast cancer as well as the differences between the characteristics in circadian rhythm changes in skin temperature data of clinically healthy and cancerous breasts and found that these changes were both definitely real and measurable.

Thermographic technology was originally introduced to complement mammography, because it was felt that a thermogram of the breast was able to detect early breast cancer development up to 10 years earlier than with most conventional modalities. However, the accuracy of thermography has remained questionable since several factors, such as the symmetry and stability of the breasts' temperature during the menstrual cycle and the use of oral contraception, have been confusing factors.

Presently, there is no ideal technique used to evaluate the results of all methods of early breast cancer detection. Studies on the use of a feasible and non invasive dynamic thermal analysis have been carried out and reported to be sensitive in detection of breast cancer. These were further enhancements with the use of the artificial neural network systems to implement a more effective thermal analysis tool. This tool had shown potential by obtaining almost 85% of sensitivity and specificity. Further studies and improvements were required to reassess this thermal analysis tool, as it may provide promising and significant contributions to the medical and research areas.

The aim of this invention is to use multiple artificial intelligence systems that analyze additional discrete thermal data points collected over a protracted period of time rather than static thermal information is more accurate and useful than current breast cancer detection modalities. This invention demonstrates the use of multiple interpretive systems bring its capabilities within the 90% specificity and sensitivity.

SUMMARY OF INVENTION

An object of the instant invention is to provide an improved device for classifying tissue of the breast.

Another object is to improve classifying tissue of the breast as to cancerous and non-cancerous conditions.

Accordingly, the invention is directed to a device for providing improved classification of breast tissue wherein the tissue is classified as one of cancerous and non-cancerous tissue. The device includes a temperature sensor for sensing temperature of a subject breast tissue over a predetermined period and generating signals in response thereto and a computer based device having hardware and software operatively associated with the temperature sensors for receiving and manipulating the signals and for applying a normalization function to each the signal. The normalization includes a function of X/Y where X is one temperature reading of a given set of readings for a particular subject and Y is the maximum temperature obtained from a predetermined number sets of temperature readings obtained a plurality of subject breast tissue from the subject, the normalization to provide a set of normalized signals and the computer based device operatively associated with a trained artificial classifier and wherein the set normalized signals are input through the trained artificial classifier to produce a signal indicative of cancerous and non-cancerous tissue of the subject.

Preferably, the computer based device is operatively associated with a plurality of trained artificial classifiers and wherein the set normalized signals are input through the trained artificial classifiers to produce signals indicative of cancerous and non-cancerous tissue of the subject. The classifier is further trained using the normalized signals. The classifiers can be selected from a group of Back-Propagation, Radial Basis Function, Gaussian Mixture Model, Fuzzy Network and Support Vector Machine.

A method for providing improved classification of breast tissue wherein the tissue is classified as one of cancerous and non-cancerous tissue includes (a) sensing temperature of a subject breast tissue over a predetermined period and generating signals in response thereto; and (b) employing a computer based device having means for receiving and manipulating the signals, applying a normalization to each the signal, the normalization including a function of X/Y where X is one temperature reading of a given set of readings for a particular subject and Y is the maximum temperature obtained from a predetermined number sets of temperature readings obtained a plurality of subject breast tissue from the subject, the normalization to provide a set of normalized signals and the computer based device operatively associated with a trained artificial classifier and wherein the set normalized signals are input through the trained artificial classifier to produce a signal indicative of cancerous and non-cancerous tissue of the subject.

BRIEF DESCRIPTION OF THE DRAWINGS

FIG. 3 depicts fluctuations of the temperature in several sensors for a patient.

FIG. 4 depicts fluctuations of the temperature in several sensors for a patient.

FIG. 5 depicts a graph of sensors temperatures at their lower values.

FIG. 6 depicts feed-forward classifier used for the four classifications.

FIG. 7 depicts a Fuzzy classification system.

FIG. 8 depicts an overview process on the SVM algorithm.

FIG. 9 depicts a comparison of ROC curves for five classifiers.

FIG. 10 depicts a graphical user interface (GUI) for detection and classification of breast cancer.

FIG. 11 depicts sample files are grouped according to patient's illness namely easy benign, difficult benign, easy cancer and difficult cancer.

DETAILED DESCRIPTION OF THE INVENTION

Figure 1:
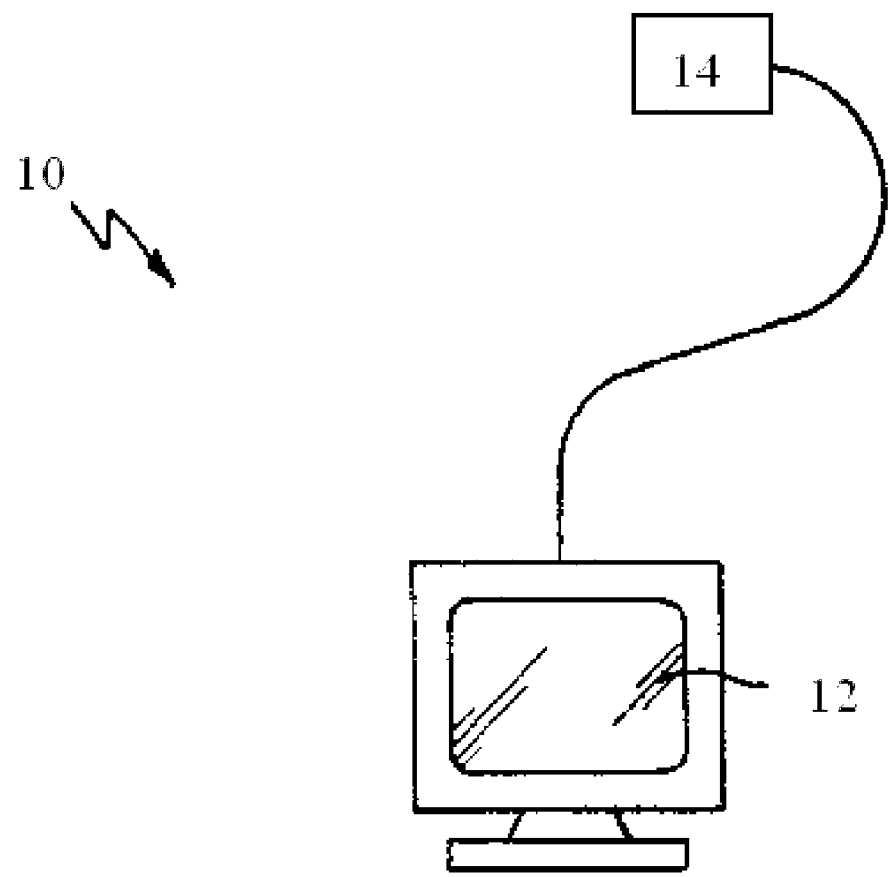
FIG. 1 is a schematic illustrating the invention.

Referring now to the drawings, the present invention is generally designated by the numeral 10. The system 10 employs use of computer-based device 12 having an operably associated memory, operating system, power source, and thermal data collecting software and which is connected to a plurality of sensors designated generally by the number 14 in FIG. 1, e.g., thermistors, wherein the sensors 14 are affixed to the breasts as illustrated in FIG. 3. There are sixteen sensors 14 which collect temperature measurements from 16 sensor locations. Eight sensors are placed on each breast in predetermined areas based on cancer development collected from a Tumor Registry and both breasts are examined concurrently. The system 10 records the temperatures for all sensors. Sensors 14 marked number 8L and 8R are reserved for placement over a suspicious lesion that is palpable.

Specifically, thermistors 1L-8L and 1R-8R are placed on the breasts as follows: 1L and 1R below the nipple; 2L and 2R in the upper outer quadrant; 3L and 3R in the upper outer quadrant toward the axilla; 4L and 4R on the upper areola; 5L and 5R on vertical midline above horizontal midline; 6L and 6R in the upper inner quadrant; 7L in an ambient temperature zone; 7R on the sternum; 28L and 28R on other areas of concern and at contralateral positions. Each pair of the thermistors (e.g., 1L/1R, 2L/2R, etc.) is preferably marked to allow for easy identification of each thermistor pair as well as each thermistor. For example, each thermistor pair is color coded and tabbed with a number and letter. Each thermistor and its signals are consequently identified with a specific position on the breast.

This consistency simplifies subsequent processing and improves accuracy of the signals in terms of individual signal correlation with calibration data and selection of specific signal sources for manipulation in developing the generalization of physiological condition. This also simplifies correlation of results with specific sensor positions on the breast to arrive at a more specific determination of the location of abnormal physiological condition. While the number of thermistors and positioning are specifically set forth, it is conceived that accuracy increases as the number of thermistors increases.

Each patient's mammogram and biopsy results, including the mammogram's finding such as suspicious of cancer or benign; the size of tumor in mm; biopsy results such as ductal carcinoma in-situ, invasive carcinoma, hyperplasia or cysts, etc. are documented separately as benchmarks for later comparison. Important details of individual patient such as age, status of menopause etc. are also collected and compiled.

Figure 2:
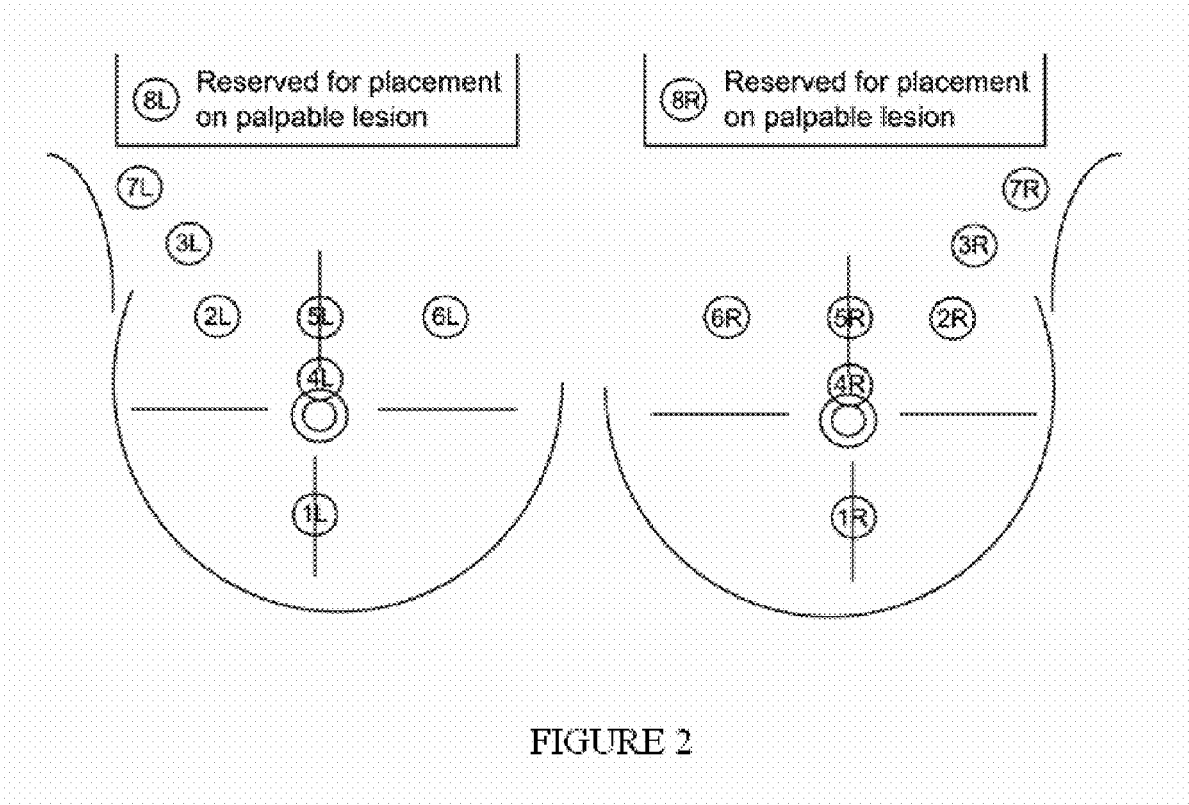
FIG. 2 shows the location of the experimental setup of sensors on a patient.

The measurement of the patients' temperatures was provided and conducted by using a microprocessor attached to sixteen thermal sensors manufacture by Yellow Springs Instrument Company. These sensors are interchangeable to within 0.01° of 1 degree centigrade and were used with a microprocessor manufactured by Lifeline Biotechnologies, Inc, Florida, USA. Thermal data measured and recorded with Lifeline's First Warning™ manufactured by Lifeline Biotechnologies, Inc, Florida, USA. There were a total of sixteen sensors, with eight sensors placed on each breast with a template designed with data from the National Tumor Registry to insure placement in the areas of the breast where the greatest number of breast cancers form. Examination was done concurrently on contralateral areas on both breasts under close monitoring for a specific period of time. FIG. 2 shows the sensors being attached to the surface of the breasts and the specific location of the sixteen sensors placed on each breast respectively.

Data Classification

The temperature readings were classified according to the results of the patients' biopsy results and diagnosis. Data were arranged in two different files, namely benign and cancer. Two files were subsequently divided into easy to detect (benign/cancer) and difficult to detect (benign/cancer) based on both the biopsy result and the location of lesion. The definitions of easy to detect (benign/cancer) and difficult to detect (benign/cancer) follow:

Easy: The leads line up with location of the lesion and the biopsy result.

Difficult: The leads line up with the location of lesion, but do not match with the biopsy result.

Data are classified according to the results of the patients' illness. There are two main categories namely benign and cancer. They are further divided into easy benign, difficult benign, easy cancer and difficult cancer as seen in FIG. 11.

However, due to need for more clarity, accuracy and ease of understanding, the classification was simplified to benign and cancer and two new classifications were added; normal and suspected cancer. Thus, there are a total of four different classifications used: normal breast, benign lesion, cancerous lesion and suspected cancer. A total of 185 patients were evaluated with the First Warning™ system. However, some of these patients were excluded from analysis due incomplete information, such incomplete: pending biopsy results and incomplete: mammography results or incomplete temperature readings files. After compilation, there were a total of 93 patients involved in this data analysis. Table 1 shows the classification of these 93 patients being categorized under the four different diagnoses groups.

TABLE 1

Patients and their classifications

| Diagnosis | Number of temperature data sets | Patient number (#) |
| --- | --- | --- |
| Normal | 1500 | #54, #88, #120 |
| Benign | 1500 | #40, #43, #46, #47, #56, #64, #68, #79, #81, #84, #92, #94, #95, #117, #122, #125, #1002, #1003, #1006, #1010, #1011, #1013, #1014, #1017, #1020, #A103, #A107, #A111, #A113, #116, #A122 |
| Cancer | 1500 | #16, #22, #32, #41, #42, #51, #60, #63, #69, #76, #82, #96, #97, #130, #145, #1001, #1004, #1005, #1018, #1022, #A104, #A105, #A114, #A115, #A117, |

TABLE 1-continued

Patients and their classifications

| Diagnosis | Number of temperature data sets | Patient number (#) |
|---|---|---|
| Suspected Cancer | 1500 | #A121, #A127, #2003, #102, #55, #87, #A108, #1016 #15, #17, #18, #20, #23, #26, #27, #31, #33, #34, #36, #37, #39, #49, #50, #53, #57, #59, #65, #86, #106, #1015, #1024 |

The 1500 sets of temperature data were randomly selected from different patients belonging to the same group. Each set of the temperature data consisted of sixteen temperature measurements collected concurrently by the sixteen sensors over the test period. There were a total of 6000 sets of temperature readings used. These were further sorted and divided into two groups; 5000 sets for training data to train each of the artificial classifier systems with the number of learning iterations being about one million per classifier and the remaining 1000 sets were used as test data. It was necessary to have more training data than testing data to allow for better training of the classifiers.

Data Inspection and Rectification

Data inspections were required to ensure that temperature readings were 'clean' of all extraneous noise' and 'abnormalities'. Inspection was done through graphical analyses by converting all the sets of temperature readings from each patient into graphs. Sixteen different colors were shown in graphic form. Each graph represented one of the sixteen sensors used for temperature measurement. If any abnormalities were found, such as great fluctuations of the temperature on a particular sensor, the patient's data would be excluded from analysis. The three graphs shown in FIGS. 3-5 respectively exhibit the abnormalities of the temperature data found in some patients. The potential causes for such phenomena are as follows:

Poor contact between the sensors and the breast surface

Continuous data recording after the screening system has shut off

Sensors dropped off from the breast surface in the midst of temperature recording FIG. 2 depicts drastic fluctuations of the temperature in several sensors for patient #1001. FIG. 3 depicts drastic fluctuations of the temperature in several sensors for patient #A116. FIG. 4 depicts all sensors having their temperatures plunge to the lower values.

Several solutions have been included in data preparation:
i. Based on the graphical analysis, manually remove the temperature reading data that has the lowest temperature during data preparation
ii. Enhancement of equipment features during the test activity an alarm has been placed on each sensor to detect abnormality during monitoring and data collection.
iii. Development of a computer program that detects those temperatures which are outside of normal range and deletes the corresponding data automatically.
iv. Apply a regression approach to select the best appropriate input data for artificial neural networks.

In this regard, a key aspect in enabling the invention was to provide a unique normalization of these temperature readings since each set of temperature readings had its own temperature range, depending on individual's health and body conditions. For example, some patients had temperature ranges from 30° C. to 35° C., while others ranged from 32° C. to 36° C. In addition, temperature ranges changed for a particular patient at different times of the day. To adjust for the different temperature ranges and to confine the correlation into a manageable range, the normalized temperature readings were used instead of the actual readings (removing statistical erroneous data prior to normalization). The temperature readings were normalized based on the following formula:

X/Y where X is the temperature variable (one temperature reading of a given set of readings for a particular subject) and Y is the maximum temperature obtained from the 3600 sets of temperature readings.

For example, 32° C.*X/Y where X is one temperature reading of a given set of readings for a particular subject and Y is 37° C.

Each reading is compared to the other 15 sets of readings. If any reading falls outside the accepted predetermined variance the data is dropped and the system instructed to go to the next set of readings, otherwise the system reads the next temp data and compares to the other sensed readings, and so on. By selection, if the difference is more than 3 degree, then system go to the end of the readings and begins with a next set of readings.

An exemplary sequence code can be as follows:
XY: Read the temp data:
Increment a counter and compare with the fifteen sets of data from each sensor. If zero, go to end, else, read the next temp data.
XX: Compare the next temp data, if the difference is more than 3 degree, go to end, Increment the counter and compare with 16. If zero go to end, else,
Jump to XX
end: jump to XY:
We also state that 5,000 training data were used train through 524
learning cycles to meet a goal of 0.000997138.
end
Read the next data.

EXAMPLE 1 INCLUDES READINGS FROM 16 SENSORS AS FOLLOWS 37.1, 37.2, 30.1, 37.4, 30.1, 37.3, 37.2, 37.4 37.1, 37.4, 37.3, 37.8, 37.6, 37.3, 37.6, 37.7

37.1, 37.2, 37.1, 37.4, 37.1, 37.3, 37.2, 37.4, 37.1, 37.2, 37.5, 37.4, 37.6, 37.3, 37.5, 37.4

37.1, 37.2, 37.3, 37.8, 37.6, 37.8, 37.6, 37.4, 37.1, 37.2, 37.5, 37.4, 37.6, 37.3, 37.5, 37.4

The 16 sensor data are arranged in this fashion in the file.
First the counter is set to 1 i.e., (C=1)
Read the first data: 37.1.
Next increment the counter. C=2
Read the next data 37.2
Compare the two reading (if less than 3), then leave this row data and go to next row. Else continue
Next increment the counter. C=3
Read the next data 30.1
Compare the present two readings. (37.2−30.1=6.9). It is greater than 3. Hence,
we need to read the next row i.e. row 2.
Now, the same thing repeats for the new row data.

EXAMPLE 2

37.1, 37.2, 37.3, 37.8, 37.6, 37.8, 37.6, 37.4, 37.1, 37.2, 37.5, 37.4, 37.6, 37.3, 37.5, 37.4

37.1, 37.2, 37.1, 37.4, 30.1, 37.3, 37.2, 37.4, 37.1, 37.2, 37.1, 37.4, 30.1, 37.3, 37.2, 37.4

37.1, 37.2, 37.5, 37.4, 37.6, 37.3, 37.5, 37.4, 37.1, 37.2, 37.3, 37.8, 37.6, 37.8, 37.6, 37.4

The 16 sensor data are arranged in this fashion in the file.

First the counter is set to 1 i.e., (C=1)

Read the first data: 37.1.

Next increment the counter. C=2

Read the next data 37.2

Compare the two reading (if less than 3), then leave this row data and go to next row. Else continue Next increment the counter. C=3

Read the next data 37.3

Compare the present two readings. It less than 3, next increment the counter. C=4

Read the next data 37.8

This process continues until C=16.

Then the new row of data is read.

The system was sufficiently trained after about 5000 iterations.

Classifiers Used

Back-Propagation Algorithm (BPA)

FIG. 5 depicts a feed-forward classifier used for the 4 classifications. Back propagation was created by generalizing the Widrow-Hoff learning rule to a multiple layer network and nonlinear differentiable transfer function. Input vectors and corresponding target vectors are used to train a network until it can approximate a function, associate input vectors with specific output vectors, or classify input vectors in an appropriate way as defined in this study. Networks with biases, a sigmoid layer and a linear output layer are capable of approximating any function with a finite number of discontinuities. The back propagation algorithm consists of two paths: the forward path and the backward path. The forward path includes creating a feed forward network, initializing weight, simulation and training the network. The network weights and biases are updated in the backward path.

The feed forward networks often have one or more hidden layers of sigmoid neurons followed by an output layer of linear neurons. Multiple layers of neurons with nonlinear transfer functions allow the network to learn nonlinear and linear relationships between input and output vectors. The linear output layer allows the network to produce values outside the range −1 to +1.

Before training a feed forward network, the weight and biases must be initialized. Random numbers around zero were used to initialize weights and biases in the network. The training process requires a set of proper inputs and targets as outputs. During training, the weights and biases of the network are iteratively adjusted to minimize the network performance function. The default performance functions for feed forward networks are the mean square errors, the average squared errors between the network outputs and the target output.

The weight update aims at maximizing the rate of error reduction, and, hence, it is termed as a 'gradient descent' algorithm. The weight increment is done in 'small' steps; the step size is chosen heuristically, as there is no definite rule for its selection. In the present case, a learning constant η=0.9 (which controls the step size) was chosen by trial and error.

The ANN structure used for the classification is shown in FIG. 6. It consists of 16 nodes to accept the data, and the two hidden layers with 17 neurons process the data using the activation function. The output layer will give rise to an output of four possible classes, whereby the network is initially trained to identify these four classes given by decoded binary output [0001 0010 0100 1000].

Radial Basis Function (RBF)

Radial basis function (RBF) networks have a static Gaussian function as the nonlinearity for the hidden layer processing elements. The Gaussian function responds only to a small region of the input space where the Gaussian is centered. The key to a successful implementation of these networks is to find suitable centers for the Gaussian functions. This action can be done with supervised learning, but an unsupervised approach usually produces better results.

The simulation starts with the training of an unsupervised layer. Its function is to derive the Gaussian centers and the widths from the input data. These centers are encoded within the weights of the unsupervised layer using competitive learning. During the unsupervised learning, the widths of the Gaussians are computed based on the centers of their neighbors. The output of this layer is derived from the input data weighted by a Gaussian mixture.

Once the unsupervised layer has completed its training, the supervised segment then sets the centers of Gaussian functions (based on the weights of the unsupervised layer) and determines the width (standard deviation) of each Gaussian. Any supervised topology (such as a multi-layer perception) may be used for the classification of the weighted input.

The advantage of the radial basis function network is that it finds the input to the output map using local approximators. Usually the supervised segment is simply a linear combination of the approximators. Since linear combiners have few weights, these networks train extremely fast and require fewer training samples.

Fuzzy Network

In a fuzzy classification system, pattern space is divided into multiple subspaces. And for each subspace, the relationships between the target patterns and their classes are described by if-then type fuzzy rules. The advantage of this system is that a nonlinear classification boundary can be easily implemented. Unknown patterns are classified by fuzzy inference, and patterns that belong to an unknown class, which is not considered by learning, can be easily rejected. Proposed methods known to the art use a simple learning procedure and a genetic algorithm (GA) to acquire a fuzzy classification system automatically. With these methods, however, a pattern space is a divided lattice-like structure. Therefore, many fuzzy rules corresponding to fine subspaces are required to implement a complicated classification boundary.

Fuzzy Classification System.

A Fuzzy classifier of the type known to the art uses subtractive clustering and a Sugeno fuzzy inference system is implemented as a classifier as shown in FIG. 7. The algorithm for implementation is as follows:

Step 1 (Fuzzify Inputs)

The input is fuzzified using symmetric Gaussian membership function given by:

$$f(x; \sigma, \mu) = \frac{e^{-(x-\mu)^2}}{2\sigma^2},$$

where $\sigma$ and $\mu$ are variance and mean, respectively

Step 2 (Fuzzy Inference)

Fuzzy inference is the process of formulating the mapping from a given input to an output using fuzzy logic for making decisions From the fuzzified inputs, the cluster centers are determined using subtractive clustering method In this method, the data point with the highest potential to be the first cluster center is selected All data points in the vicinity of the first cluster center (as determined by radii) are removed in order to determine the next data cluster and its center location This process is iterated until all of the data is within the radii of a cluster center Step 3 (Obtaining the Membership Computation)

Final output is obtained using the Sugeno fuzzy model. The output membership function is linear and is given by r=ax+by+cz+d, where a, b, c, d are the adaptive parameters The output level $r_i$ of each rule is weighted by the firing strength $w_i$ of the rule. The final output of the system is the weighted average of all rule outputs and is computed as $$\text{Final Output} = \frac{\sum_{i=1}^{N} w_i r_i}{\sum_{i=1}^{N} w_i},$$

where N=the total number of fuzzy rules

Gaussian Mixture Model (GMM)

A Gaussian Mixture Model (GMM) is a parametric model used to estimate a continuous probability density function from a set of multi-dimensional feature observations. It is widely used in data mining, pattern recognition, machine learning and statistical analysis. This Gaussian mixture distribution can be described as a linear superposition of K multidimensional Gaussian components given by:

$$p(x) = \sum_{k=1}^{K} \pi_k N\left(x \mid \mu_k, \sum_k\right)$$

where $\pi_k$, $\mu_k$, $\Sigma_k$ are mixing coefficients, mean and covariance respectively.

The solution for determining the parameters of GMM is estimated by using the maximum likelihood (ML) criterion. A powerful method for maximizing the likelihood solution models is by the general form of Expectation-Maximization (EM) algorithm. The steps to carry out the EM algorithm are as followed:

i. Initialize the means $\mu_k$, covariances $\Sigma_k$ and mixing coefficients $\pi_k$, and evaluate the initial value of the log likelihood.

ii. E step: Evaluate the responsibilities using the current parameter values $$\gamma(z_{nk}) = \frac{\pi_k N\left(x_n \mid \mu_k, \sum_k\right)}{\sum_{j=1}^{K} \pi_j N\left(x_n \mid \mu_j, \sum_j\right)}$$

iii. M step: Re-estimate the parameters using the current responsibilities $$\mu_k^{new} = \frac{1}{N_k} \sum_{n=1}^{N} \gamma(z_{nk}) x_n$$

$$\sum_k^{new} = \frac{1}{N_k} \sum_{n=1}^{N} \gamma(z_{nk})(x_n - \mu_k^{new})(x_n - \mu_k^{new})^T$$

$$\pi_k^{new} = \frac{N_k}{N}$$

where $$N_k = \sum_{n=1}^{N} \gamma(z_{nk})$$

iv. Evaluate the log likelihood and check for convergence of either the parameters or the log likelihood. If the convergence criterion is not satisfied return to Step (ii).

$$\ln p(X \mid \mu, \Sigma, \pi) = \sum_{n=1}^{N} \ln \left\{ \sum_{k=1}^{K} \pi_k N\left(x_n \mid \mu_k, \sum_k\right) \right\}$$

However in EM algorithm, it takes more iteration to reach convergence compared with the K-means algorithm, and each cycle needs more computation. Hence, it is common to use the K-means algorithm to find the initial estimates of the parameters obtained from a sample of the training data. The K-means algorithm uses the squared Euclidean distance as the measure of dissimilarity between a data point and a prototype vector. This not only limits the type of data variables to be considered but also makes the determination of the cluster means non-robust to the outliers. This algorithm starts off by choosing randomly the initial means and assumed unit variances for the diagonal covariance matrix which is being adopted in the current work.

One of the important attributes of the GMM is its ability to form smooth approximations for any arbitrarily-shaped densities. As 'real world' data has multi-modal distributions, GMM provide an extremely useful tool to model the characteristics of the data. Another similar property of GMM is the possibility of employing a diagonal covariance matrix instead of a full covariance matrix. Thus, the amount of computational time and complexity can be reduced significantly. GMMs have been widely used in many areas of pattern recognition and classification, with great success in the area of speaker/voice identification and verification.

Support Vector Machine (SVM)

In the recent years, Support Vector Machine (SVM) classifiers have demonstrated excellent performance in a variety of pattern recognition problems. The methodology is known in the art. SVM is known as the "nonparametric" model in which parameters that define the capacity of the model are data-driven in such a way as to match the model capacity to data complexity. It is developed in reverse order compared to the development of neural networks (NNs), as the value of the training error is being fixed and the confidence interval is minimized. However in NNs, the appropriate structure of the model is being chosen, estimation error is fixed and the training error is being minimized.

The SVM is a supervised learning method that generates input-output mapping functions from a set of labeled training data. The mapping function can be either a classification function or a regression function. For classification, nonlinear kernel functions are often used to transform input data to a high-dimensional feature space in which the input data become more separable compared to the original input space. Maximum-margin hyper-planes are then created; hence, the model produced depends on only a subset of the training data near the class boundaries. This classification method is currently adopted in the current work.

The aim of SVM modeling is to find a separating hyperplane which separates positive and negative examples from each other with optimal margin; in other words, the distance of the decision surface and the closest example is maximal as shown in FIG. 8. Essentially, this involves orienting the separating hyperplane to be perpendicular to the shortest line separating the convex hulls of the training data for each class, and locating it midway along this line. The vectors that constrain the width of the margin are the support vectors. FIG. 7 depicts an overview process on SVM algorithm.

Let the separating hyperplane be defined by $x \cdot w + b = 0$, where w is its normal. For linearly separable data labeled $\{x_i, y_i\}$, $x_i \in \Re^{V_d}$, $y_i = \{-1, 1\}$, $i = 1, \ldots, N$, the optimum boundary chosen with maximal margin criterion is found by minimizing the objective function:

$$E = \|w\|^2 \quad (1)$$

Subject to $(x_i \cdot w + b) y_i \geq 1$, for all i.

The solution for the optimum boundary $w_0$ is a linear combination of a subset of the training data, $s \in \{1 \ldots N\}$: the support vectors. These support vectors define the margin edges and satisfy the equality $(x_s \cdot w_0 + b) y_s = 1$. Data may be classified by computing the sign of $x \cdot w_0 + b$.

Generally, the data are not separable, and the inequality in the equation (1) cannot be satisfied. In this case, a "slack" variable $\xi_i$ that represents the amount by which each point is misclassified is introduced. The new objective function is now reformulated as $$E = \frac{1}{2}\|w\|^2 + C \sum_i L(\xi_i) \quad (2)$$

Subject to $(x_i \cdot w + b) y_i \geq 1 - \xi_i$ for all i.

The second term on the right-hand side of equation (2) is the empirical risk associated with those points that are misclassified or lie within the margin. L is a cost function and C is a hyper-parameter that trades-off the effects of minimizing the empirical risk against maximizing the margin. The first term can be thought of as a regularization term, deriving from maximizing the margin, which gives the SVM its ability to generalize well on sparse training data.

Kernel functions can be used to extend to solution of nonlinear boundaries problems. Kernel functions define a nonlinear mapping from the input space (observed data) to a manifold in higher dimensional feature space, which is defined implicitly by the kernel functions. The hyperplane is constructed in the feature space and intersects with the manifold, creating a nonlinear boundary in the input space. In practice, the mapping is achieved by replacing the value of the dot products between two vectors in the input space with the value that results when the same dot product is carried out in the feature space. The dot product in the feature space is expressed by functions (i.e., the kernels) of two vectors in input space. The polynomial and radial basis function (RBF) kernels are commonly used, and they are $$K(x_i, x_j) = (x_i \cdot x_j + 1)^n \quad (5)$$

and $$K(x_i, x_j) = \exp\left[-\frac{1}{2}\left(\frac{\|x_i - x_j\|}{\sigma}\right)^2\right] \quad (6)$$

Respectively, where n is the order of the polynomial and $\sigma$ is the width of the RBF, the dual for the nonlinear case is given by:

$$\alpha^* = \max_\alpha \left( \sum_i \alpha_i + \sum_{i,j} \alpha_i \alpha_j y_i y_j K(x_i \cdot x_j) \right) \quad (7)$$

Subject to $$0 \leq \alpha_i \leq C$$

$$\sum_i \alpha_i y_i = 0$$

With the above formulation on the use of kernels, an explicit transformation of the data to the feature space is not required. Several algorithms extend the basic binary SVM classifier to be a multi-class classifier. Examples consist of one-against-one SVM, one-against-all SVM, half against half SVM and Directed Acyclic Graph SVM (DAGSVM).

Results

In testing the five classifiers, at least 1000 sets of test data to compare on the performance of the classifiers. The following Table 2 shows the performance of the five classifiers used for classification.

TABLE 2

Comparison on the percentage of correct classification for the classifiers.

| Type of classifiers | No of training data used | No of testing data used | Percentage (%) of correct classification |
|---|---|---|---|
| BPA | 5000 | 1000 | 83.1 |
| RBF | 5000 | 1000 | 86.1 |
| Fuzzy | 5000 | 1000 | 77.4 |
| GMM | 5000 | 1000 | 90.6 |
| SVM | 5000 | 1000 | 85.6 |
| | | AVERAGE | 84.5 |

All five classifiers managed to obtain approximately 85% of correct classification. BPA classifier was trained under 2 hidden layers of 17 neurons. In FIG. 6, it shows the four layers feed-forward structure of BPA neural network. 5000 training data were successfully trained after going through 524 learning cycles to meet a goal of 0.000997238.

However, the BPA classifier was only able to classify the unknown data correctly with an accuracy of 83.1%. Among these five classifiers, GMM had the best performance, as it had obtained the highest percentage of correct classification of 90.6%, whereas RBF, Fuzzy and SVM obtained 86.1%, 77.4% and 85.6% of accuracy, respectively. The performance of the five classifiers was evaluated using the following three performance indices.

Sensitivity
Specificity
Positive predictive value

Sensitivity of a test is the proportion of people with the disease who have a positive test result, the higher the sensitivity, the greater the detection rate and the lower the false negative (FN) rate. The specificity of the test is the proportion of people without the disease who have a negative test, the higher the specificity the lower will be the false positive rate and the lower the proportion of people who have the disease who will be unnecessarily worried or exposed to unnecessary treatment. The positive predictive value (PPV) of a test is the probability of a patient with a positive test actually having a disease.

Receiver Operating Characteristics (ROC) Analysis

The ROC curve is a plot of sensitivity against (1-specificity). Sensitivity, also known as true positive fraction (TPF), refers to the probability that a test result was positive when the disease was present.

The area under the ROC curve indicates the performance of the classifier across the entire range of cut-off points. Conventionally, the area under the ROC curve must range between 0.5 and 1. If the area was closer to 1, this showed that the classifier had better accuracy in the testing. Currently, the area under the ROC curve is the best indicator for the classifier's performance with regard to the misclassification rate and the measure of risk based on confusion and loss matrices. This is because ROC was able to provide the most complete way of quantifying the diagnostic accuracy.

MedCalc™ statistical software was used for this analysis. The ROC results based on the sensitivity, specificity, positive predictive value and area under curve for the three classifiers were tabulated in Table 3

TABLE 3

Results of Performance Indices for the five classifiers used.

| Classifier | TN | TP | FP | FN | Sensitivity (%) | Specificity (%) | Area under the curve | +PV |
|---|---|---|---|---|---|---|---|---|
| BPA | 209 | 622 | 41 | 128 | 82.9 | 83.6 | 0.833 | 93.8 |
| RBF | 195 | 666 | 55 | 84 | 88.8 | 78 | 0.834 | 92.4 |
| Fuzzy | 189 | 585 | 61 | 165 | 78 | 75.6 | 0.768 | 90.6 |
| GMM | 195 | 711 | 55 | 39 | 94.8 | 78 | 0.864 | 92.8 |
| SVM | 226 | 630 | 24 | 120 | 84 | 90.4 | 0.872 | 96.3 |

The results obtained from the 1000 testing data were classified under true negative (TN), true positive (TP), false positive (FP) and false negative (FN), depending on each classifier's situation. As shown in Table 3, the GMM classifier showed the highest sensitivity of 94.8% among the five classifiers. This was followed by RBF and SVM with sensitivity of 88.8% and 84% respectively. This observation had showed that the higher sensitivity of the classifier would result in a greater detection rate by causing the false negative rate to be lower.

SVM showed the highest specificity of 90.4%, and this was justified by the number of true negative cases. This result was followed by BPA with specificity of 83.6%, and both GMM and RBF had the same specificity of 78%. Fuzzy showed the least specificity 75.6%. In tabulating the positive predictive value, SVM classifier showed the highest value of 96.3, followed by BPA with value of 93.8 The PPV values for GMM, RBF and fuzzy were 92.8, 92.4 and 90.6 respectively.

The area under the curve is also an important parameter as it determines the overall classification accuracy for the five classifiers. FIG. 9 illustrates the comparison of the ROC curve for the five classifiers. The SVM (purple dotted line) had the largest area under the curve, whereas fuzzy (pink line)'s area was the smallest among the five classifiers. This result was reinforced based on the area under the curve tabulated in Table 3. It was accountable for SVM to have an area of 0.872 which is the largest area under the curve as compared to the other four classifiers with an area 0.768, 0.833, 0.834 and 0.864 (Fuzzy, BPA, RBF and GMM), respectively. As seen from the results obtained, SVM was the most accurate classifier due to its area being closer to 1.

In this statistic analysis of ROC curves, SVM was considered the outstanding classifier, even though GMM had achieved the highest sensitivity. This result was based on the four performance indices in which SVM had attained the best result in three of these indices. SVM had the greatest specificity and positive predictive value and had also attained the largest area under the curve which implies its accuracy. Therefore, SVM was considered to be an excellent classifier.

FIG. 8 Comparison of ROC Curves for the Five Classifiers.

Graphical User Interface (GUI)

A snap shot of the graphical user interface (GUI) is shown in FIG. 10. FIG. 10 Graphical User Interface (GUI) for detection and classification of breast cancer. The procedures for the Graphical User Interface were carried out by firstly uploading the set of temperature data required to be classified. This action was done by clicking on the push button labeled 'Upload data'. Once the data has been selected, the file name will appear on the 'Input' text box. After this, the user may select any of the five classifiers which they wish to test, for instance Back-Propagation Algorithm (BPA) or Gaussian Mixture Model (GMM). The various stages of breast cancer are represented by the four different images, namely; Normal, Benign, Cancer and Suspected-Cancer. Colors are also being used to identify the various stages of breast cancer.

The classified result will be shown in the output classification section. For instance, if the classified result is 'Cancer,' the box next to it will turn pink which represents 'Cancer' as shown in the color indicator. The image which represents 'Cancer' will also be highlighted in the stages of breast cancer. Under the output classification, there is another section which allows us to view the results obtained by the other algorithms used. The classified result will be based on the result from the majority of the algorithms. For instance, if the result shown for most of the algorithms is 'Cancer,' then the classified result will be shown as 'Cancer.' Lastly, the whole procedure can be repeated by clicking on the push button 'Reset' in order to use another classifier or to input new data. The Graphical User Interface designed is user-friendly as it is simple and easy to use.

Mammography is the most commonly used screening tool for breast cancer. It has high sensitivity, but can distinguish the benign from malignant lesions only up to 55%. Limitations of mammography include the inability to evaluate the radiographically dense breast, common in Asian or younger women, and the postoperative breast, where scar is difficult to distinguish from recurrent tumor. Additionally, it has been shown that magnetic resonance imaging (MRI) was more accurate than ultrasonography and mammography in measuring the largest cancer diameters in women having larger cancers.

This instant invention reveals that the use of temperature as a tool to detect breast cancer is possible though the performance of the current discrete temperature approach will improve the addition of further training data, since all of these classifiers are iterative and improve in their accuracy as more data is added, especially for much younger females who are not suitable for mammogram.

By virtue of the normalization technique described above and through employing the variety of classifiers which are used in an iterative training process of upwards of a million iterations, the inventor has improved the percentage of the correct classification by using such classifiers and efficient preprocessing techniques.

The accuracy of the instant invention is increased by increasing the size and quality of the training set. The classification software for the different classes is written in MATLAB™ 7.0.4 known in the art.

In this invention, an interpretive system has been developed and implemented for the detection and classification of the breast cancer patients. This system incorporated dynamic thermal analysis and analytical software to produce a potential tool for detection of breast cancer. Five classifiers; namely, back-propagation algorithm, radial basis function, fuzzy, Gaussian mixture model and support vector machine were used for decision-making. The accuracy of these classifiers generally depends on the size and quality of the training data, the rigor of the training imparted and also the parameters used to represent the input (breast surface temperature). With more temperature data being analyzed in this work, the five classifiers were able to achieve more than 90% of accuracy in classifying the four different diagnoses (normal, benign, cancer and suspected-cancer). Among the five classifiers used, the GMM was able to produce the highest percentage of correct classification for unknown data and sensitivity. A significant advantage of the artificial neural network system of classifiers is that the system provides a detection system without human interpretation or human error. Using five separate methods of analyzing data from five independent classifiers, positive predictive values can provide a picture of the underlying physiology of the breast and not an interpretation of images.

The above described embodiments are set forth by way of example and are not for the purpose of limiting the present invention. It will be readily apparent to those skilled in the art that obvious modifications, derivations and variations can be made to the embodiments without departing from the scope of the invention. Accordingly, the claims appended hereto should be read in their full scope including any such modifications, derivations and variations.

What is claimed is:

1. A device for providing improved classification of breast tissue wherein the tissue: is classified as one of cancerous and non-cancerous tissue, which comprises:
    means for sensing temperature of a subject breast tissue over a predetermined period and generating signals in response thereto;
    means operatively associated with said means for sensing for receiving and manipulating said signals employing a computer based device operatively associated with means for applying a normalization to each said signal, said normalization including a function of X/Y where X is one temperature reading of one of said signals for a particular subject and Y is the maximum temperature obtained from a predetermined number sets of temperature readings obtained a plurality of subject breast tissue from said subject, said normalization to provide a set of normalized signals and said computer based device operatively associated with a trained artificial classifier and wherein said set normalized signals are input through said trained artificial classifier to produce a signal indicative of cancerous and non-cancerous tissue of the subject.

2. The device for providing improved classification of breast tissue of claim 1, wherein said computer based device is operatively associated with a plurality of trained artificial classifiers and wherein said set normalized signals are input through said trained artificial classifiers to produce signals indicative of cancerous and non-cancerous tissue of the subject.

3. The device for providing improved classification of breast tissue of claim 1, wherein said classifier is further trained using said normalized signals.

4. The device for providing improved classification of breast tissue of claim 2, wherein said classifiers are selected from a group of Back-Propagation, Radial Basis Function, Gaussian Mixture Model, Fuzzy Network and Support Vector Machine.

5. A method for providing improved classification of breast tissue wherein the tissue is classified as one of cancerous and non-cancerous tissue, which comprises:
    (a) sensing temperature of a subject breast tissue over a predetermined period and generating signals in response thereto;
    (b) employing a computer based device having means for receiving and manipulating said signals, applying a normalization to each said signal, said normalization including a function of X/Y where X is one temperature reading of a given set of readings for a particular subject and Y is the maximum temperature obtained from a predetermined number sets of temperature readings obtained a plurality of subject breast tissue from said subject, said normalization to provide a set of normalized signals and said computer based device operatively associated with a trained artificial classifier and wherein said set normalized signals are input through said trained artificial classifier to produce a signal indicative of cancerous and non-cancerous tissue of the subject.

6. The method for providing improved classification of breast tissue of claim 5, wherein said computer based device is operatively associated with a plurality of trained artificial classifiers and wherein said set normalized signals are input through said trained artificial classifiers to produce signals indicative of cancerous and non-cancerous tissue of the subject.

7. The method for providing improved classification of breast tissue of claim 5, wherein said classifier is further trained using said normalized signals.

8. The method for providing improved classification of breast tissue of claim 6, wherein said classifiers are selected from a group of Back-Propagation, Radial Basis Function, Gaussian Mixture Model, Fuzzy Network and Support Vector Machine.

* * * * *